United States Patent [19]

Bentley et al.

[11] 3,989,626
[45] Nov. 2, 1976

[54] MEMBRANE TRANSFER PROCESS AND APPARATUS

[75] Inventors: Donald J. Bentley, Newport Beach; Donald A. Raible, Orange, both of Calif.

[73] Assignee: Bentley Laboratories, Inc., Irvine, Calif.

[22] Filed: Dec. 30, 1974

[21] Appl. No.: 537,577

Related U.S. Application Data

[63] Continuation of Ser. No. 364,947, May 29, 1973, abandoned.

[52] U.S. Cl. ............................. 210/177; 210/321 B
[51] Int. Cl.² .......................................... B01D 31/00
[58] Field of Search ............... 23/258 J; 210/22, 23, 210/321, 177

[56] References Cited
UNITED STATES PATENTS

| | | | |
|---|---|---|---|
| 3,228,876 | 1/1966 | Mahon | 210/321 X |
| 3,332,746 | 7/1967 | Claff et al. | 210/321 X |
| 3,557,962 | 1/1971 | Kohl | 210/321 |
| 3,704,223 | 11/1972 | Dietzsch et al. | 204/301 |

*Primary Examiner*—Frank A. Spear, Jr.
*Attorney, Agent, or Firm*—Lyon and Lyon

[57] ABSTRACT

The present invention relates to a tubular membrane apparatus, which may be made as a disposable unit, and the method of operation of that apparatus to achieve a transfer or exchange function. More specifically, the present invention may be used to oxygenate blood, purify water, as a dialysis medium, and for other purposes. The apparatus comprises a series of tubular membranes which are deformed at spaced intervals along their lengths to induce turbulent flow and secondary flow patterns which displace the stationary boundary layer which would otherwise exist adjacent to the inner surface of the tubular membrane such that the resistance to diffusion or exchange is substantially reduced. Pulsatile flow of the fluid within the tubular membrane and/or the fluid surrounding the tubular membrane may be employed to enhance the effectiveness of the unit. In a preferred embodiment, a liquid is flowed through the tubular membranes and a gaseous medium is caused to flow around the outer surface of the tubular membrane.

7 Claims, 10 Drawing Figures

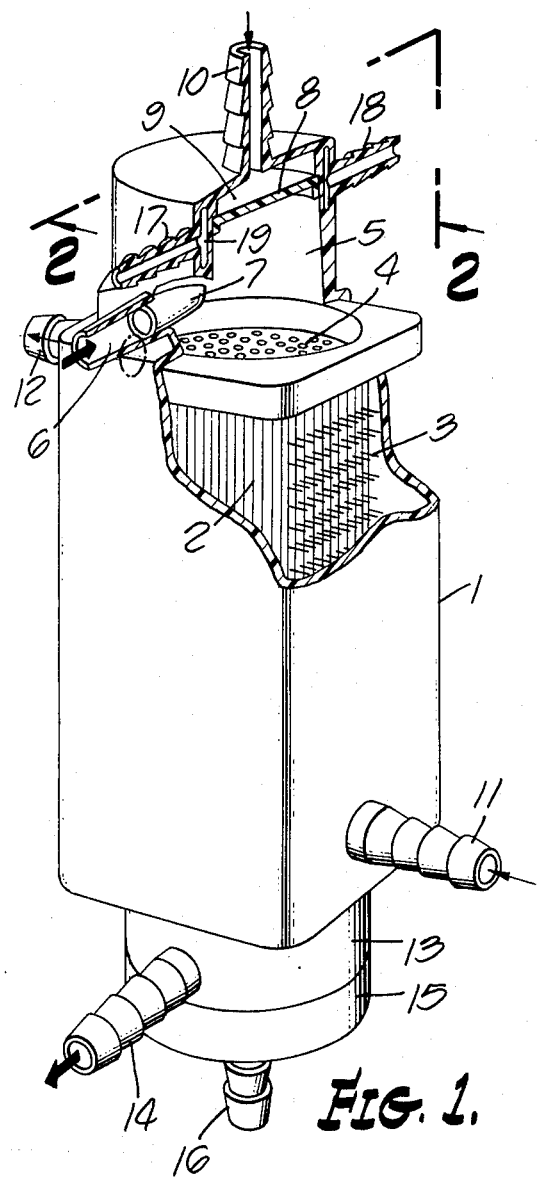
FIG. 1.
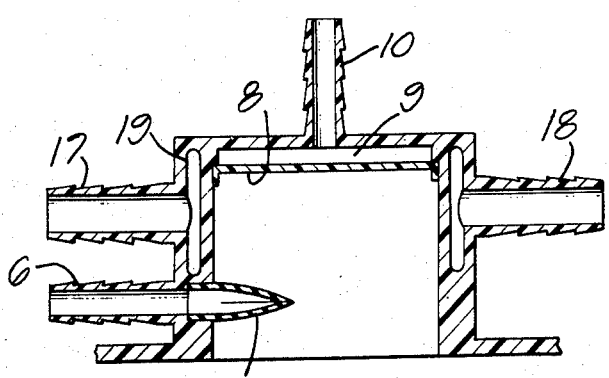
FIG. 2.
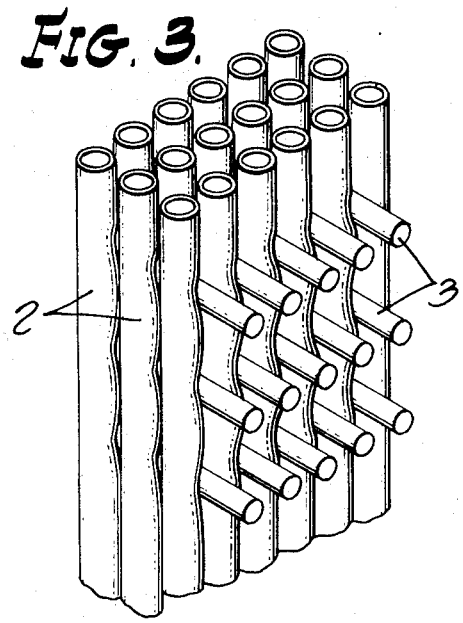
FIG. 3.
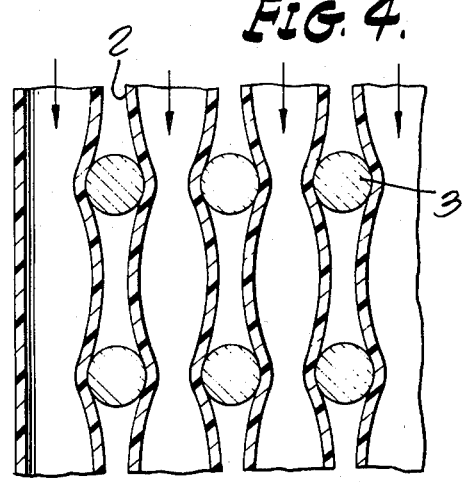
FIG. 4.
FIG. 5.

MEMBRANE TRANSFER PROCESS AND APPARATUS

This is a continuation of application Ser. No. 364,947, filed May 29, 1973, now abandoned.

BACKGROUND OF INVENTION

The use of semi-permeable membranes to accomplish various fluid exchange, removal or diffusion functions has been known for some time, e.g., in the fields of salt-water purification, dialysis and gas exchange. More specifically there has been some application of such technology to blood oxygenators, e.g., U.S. Pat. No. 3,332,746, the disclosure of which is incorporated by reference herein, which function to maintain the desired oxygen-carbon dioxide balance in blood when the cardiorespiratory system is not totally capable of doing so. However, the most widely used blood oxygenators at the current time are those of the bubbler type in which oxygen is introduced into blood through small diameter orifices such that bubbles are formed in the blood. Exemplary disclosures of bubbler type blood oxygenators may be found in U.S. Pat. Nos. 3,265,883; 3,468,631; 3,488,158, and 3,578,411, the disclosures of which are incorporated by reference herein. Theoretically, membrane oxygenators would possess certain advantages as compared to bubbler type or disc type oxygenators including reduction of the risk of trauma to the blood, but the membrane oxygenators presently available for use do not enjoy widespread use because of inefficient diffusion transport rates, relatively large blood priming volumes and high cost due, among other things, to difficulty of assembly.

In order to accomplish gas transfer through a membrane, it is necessary to overcome the resistance created by two principal causes, namely, the membrane itself and the liquid layer on the surface of the membrane. In a blood oxygenator, the blood which is to be oxygenated is on one side of the membrane and the oxygen which is to be diffused into the blood is on the other and the membrane is gas pervious but blood impervious. In membrane oxygenators of the type currently being clinically used, it is estimated that about 60% to 85% of the resistance to diffusion of oxygen and carbon dioxide (the latter being removed from the blood) is caused by the blood film which forms on the surface of one side of the membrane. Typically such oxygenators employ silicone rubber alone or in combination with other materials as the membrane material.

Various approaches have been employed in attempts to overcome the boundary layer resistance of the blood to gas diffusion. Among them have been the use of extremely small diameter tubular membrane configurations, on the order of $100\mu$ to $300\mu$, reduce the size of the blood film. However, several thousand such capillary-size tubes are required to accommodate the necessary blood volume and the small size creates a risk of thrombus formation. A variation of this approach is to place an even smaller diameter tube within a capillary tube such that the blood flows in the annular space between them and, by using pulsatile blood and gas flows, some reduction in boundary layer effects is achieved.

Another capillary flow technique includes the use of flat sheet membranes enveloping plates having capillary grooves therein.

Various attempts to reduce boundary layer effects by inducing turbulent flow to displace the boundary layer include the use of torsionally oscillating toroidal membrane chambers.

Reduction of the thickness of the liquid film has been attempted by the use of sheet membranes over separater plates having capillary furrows extending transversely to or with the direction of blood flow and by the use of pulsatile or steady gas and/or blood flows. Another approach has been the use of a plurality of tubular membranes enclosed in a flexible sleeve which sleeve is pulsed to induce blood blow within the tubular membranes.

The foregoing approaches have required the use of bulky external supporting equipment, achieved only marginal improvement in diffusion or have otherwise been subject to disadvantages such that only a minor proportion of clinical oxygenator use has involved membrane type units. In this regard, the desirability that such oxygenators be of the disposable type should also be noted, since several of the foregoing approaches do not lend themselves to disposability.

THE PRESENT INVENTION

The present invention comprises a tubular membrane apparatus, which may be made as a disposable unit, and the method of operation of that apparatus. Broadly, the apparatus of the present invention comprises a plurality of tubular membranes of relatively large diameter, preferably about ⅛ inch to ⅜ inch, which are shaped in such a manner as to induce turbulent flow of the fluid within them, and minimize the pressure drop through the device. In a preferred embodiment, this shaping is achieved by positioning a series of rods such that they deform a portion of the walls of the tubes. The secondary flow which results from such deformation reduces the resistance to diffusion of the fluid in the tube by a mixing and churning action which allows access to the membrane walls of substantially more fluid within the tube than would otherwise be the case. This more efficient use of membrane surface permits the use of larger diameter tubes than would otherwise be possible thereby reducing hydraulic differential pressure over the length of the tube to relatively low levels. The larger diameter tubes also reduce the danger of thrombus formation and permits using fewer tubes thereby reducing the overall size of the unit and the priming volume required.

The shape of the rod, the frequency and pattern of deformations along the length of the tubes, the diameter of the tubes, and the nature of the membrane material will depend upon the fluids passing through the tubes and around their outer surfaces, as well as the volume and rate of fluid flow desired. However, given the principles of the present invention, only routine experimentation will be required to correlate fluid rate, fluid volume, and path configuration. Such determinations will, of course, in the usual case be made after a membrane material has been selected. If the unit is to be used for blood oxygenation, various membranes of the type previously used in membrane blood oxygenators may be used, but asymetric membranes of the type disclosed in U.S. patent application Ser. No. 347,156, filed Apr. 2, 1973, entitled "MICROPOROUS POLYESTER MEMBRANES AND POLYMER ASSISTED PHASE INVERSION PROCESS FOR MAKING SAME," the disclosure of which is incorporated herein by reference, have been found particularly suitable. On the other hand, when the unit is to be used for water purification, cellulose acetate membranes or other membranes of the type disclosed in U.S. Pat. Nos. 3,133,132; 3,133,137; and 3,457,170, the disclosures of which are incorporated by reference herein, may be used. If the unit is to be used in dialysis, e.g., as an artificial kidney, the membranes known to those skilled in the art may be used or, preferably, membranes of the type disclosed in U.S. patent application Ser. No. 347,156, above, may be used.

Still further, deformation of the tubular membranes may be achieved in whole or in part by twisting the tubular membrane. For example, the tubular membrane may be partially flattened such that it has a generally elliptical cross section and then helically twisted along its entire length or at spaced intervals along its length. Still further, such twisting may be used in conjunction with deformation caused by rods in the manner discussed above.

With regard to the rods used to deform the tubular membranes, rods having circular cross sections are believed to be satisfactory for most purposes, but the cross section of the rod may be varied according to the particular flow characteristics desired and the rods may be elliptical, generally rectangular, or other shapes. It is, of course, usually desirable to avoid sharp corners to reduce the possibility of membrane damage. When the apparatus of the present invention is used as a blood oxygenator, it is believed that the spacing between adjacent banks of rods will desirably be about twice the diameter of the membrane tubes and the construction of the diameter of the tubular membrane will be about 50–90% of the undeformed diameter. It is further believed that the desirable radius of curvature of deformation of the membrane tubes will be about the same as the diameter of those tubes.

It will be apparent from the foregoing, that it is an object of this invention to provide a membrane apparatus and processes for fluid diffusion and exchange which increase the efficiency of operation by reducing the boundary layer effects which create resistance to the desired exchange or diffusion. It is another object of this invention to increase the efficiency of such apparatus and processes by means of the configuration of the flow path through tubular membranes such that secondary flow effects and/or turbulence will displace the boundary layer which would otherwise exist undisturbed at the inner surface of the tubular membrane.

DESCRIPTION OF THE DRAWINGS

FIG. 1 is a perspective view of an embodiment of the apparatus of the present invention.

FIG. 2 is a cross-sectional view of the inlet portion of the apparatus of FIG 1.

FIGS. 3–10 are cross-sectional and perspective views of various arrays of tubular membranes and deforming rods which may be used in the apparatus of the present invention.

Figure 6:
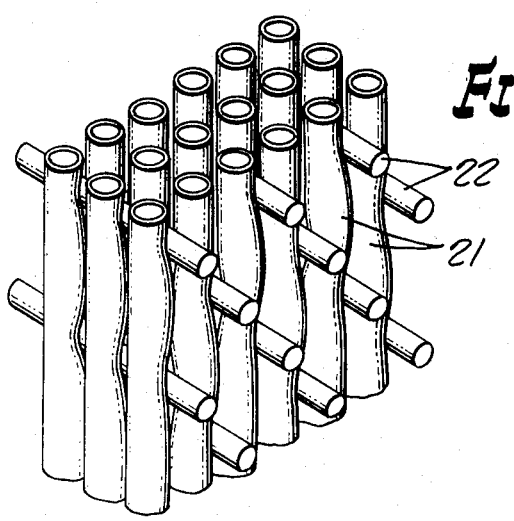

As shown in the drawings, a preferred embodiment of the apparatus of the present invention, as shown in FIG. 1, comprises a housing 1 enclosing a plurality of tubular membranes 2. A plurality of rods 3 are arrayed at spaced intervals between the tubular membranes. One end 4 of the group of tubular membranes 2 terminates in one wall of and opens into an inlet chamber 4. For purposes of clarity, this description of the apparatus will assume that it is to be used as a blood oxygenator. Inlet chamber 5 is provided with a blood inlet port 6 which is provided with a unidirectional control means which is illustrated as a leaf nozzle but which may be a check valve or other suitable means for permitting flow of blood into the inlet chamber 5 but not back out of port 6. One wall of inlet chamber 5 is formed by flexible diaphram 8. Diaphram 8 also forms one wall of pressure chamber 9 which is connected through port 10 to a source of pulsatile pressure, e.g., a variable source of pneumatic or hydraulic pressure, not shown. Housing 1 is also provided with gas inlet means 11 and gas vent means 12 as well as outlet chamber 13. The latter is provided with blood outlet port 14 which is also provided with a unidirectional flow means such as element 7 which permits flow out of said outlet chamber through port 14 but not back into outlet chamber 13 through port 14. A second pressure chamber 15 provided with port 16 which communicates with a source of pulsatile pressure (not shown) is provided in association with outlet chamber 13 in the same manner that inlet chamber 5 and pressure chamber 9 are associated. Inlet chamber 5 is also provided with means for heat exchange comprising heat exchange medium inlet port 17, outlet port 18, and circulation chamber 19. These same elements are shown in cross-section in FIG. 2.

Outlet chamber 13 may be provided with heat exchange means in the same manner. Tubular membranes 2 and deforming rods 3 are shown in somewhat more detail in perspective view in FIG. 3 and in cross-sectional view in FIG. 4.

Figure 7:
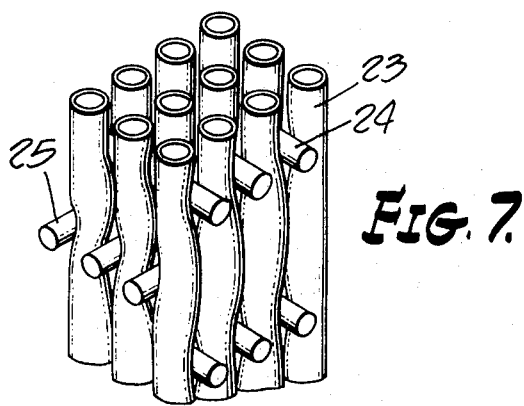
Figure 8:
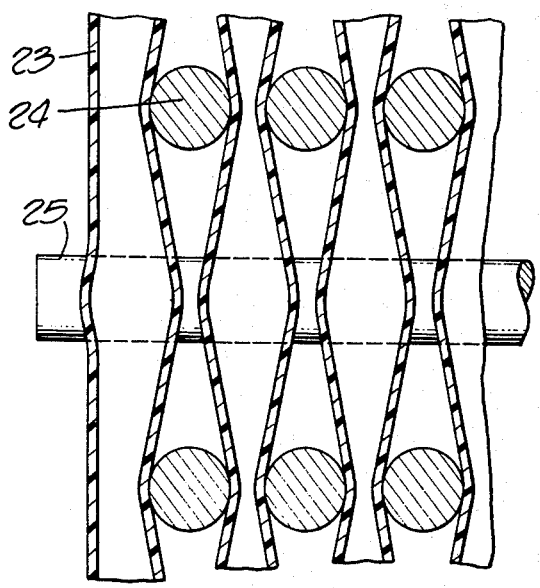

FIG. 5 illustrates the same general assembly as FIG. 4 with the exception that pins 20 are elliptical in cross-section. FIG. 6 illustrates tubular membranes 21 and pins 22 in staggered relationship whereas FIGS. 7 and 8 illustrate, in perspective and cross-section respectively, an arrangement in which tubular membranes 23 are deformed by banks of rods 24 and 25 which are perpendicular with relation to each other.

Figure 9:
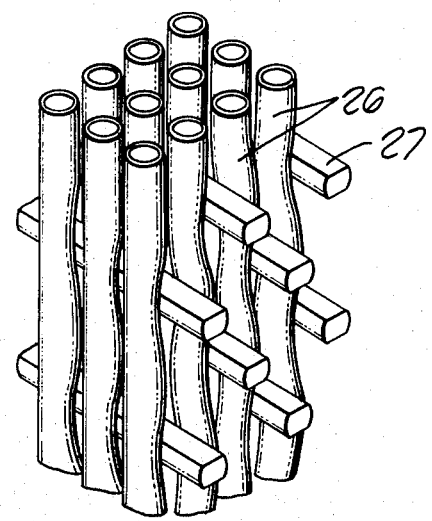
Figure 10:
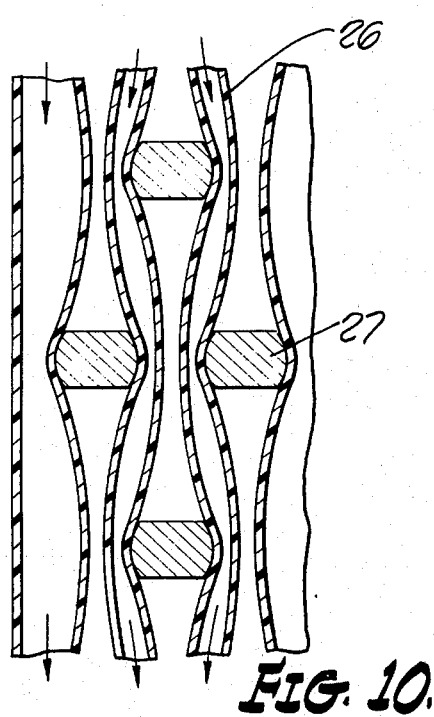

Similarly, FIGS. 9 and 10 illustrate the deformation of tubes 26 by rods having a generally rectangular cross-section.

In operation, the blood oxygenator described above may be attached directly to the veins of the patient or to a separate blood supply and the blood may be introduced into the apparatus by gravity, by pumping, or by a combination of the two. In the embodiment shown, the venous blood is introduced through port 6 and unidirectional valve 7 into inlet chamber 5 in a direction orthogonal to the rows of tubular membranes 2. The blood is then forced into the tubular membranes either by application of external pressure on diaphram 8 or by pumping at continuous or pulsatile flow. Blood then flows through the tubular membranes while oxygen is admitted through gas inlet port 11 and flows around the tubular membranes. Diffusion takes place through the walls of the membranes whereby oxygen passes into the blood and carbon dioxide passes out of the blood and through the walls of the membrane. Excess oxygen together with carbon dioxide and water vapor are discharged through port 12. The oxygenated blood flows out of port 14 and either directly into the patient or into a blood pump. The blood flow may be controlled by the pulsing of one or both diaphrams in the blood inlet and blood outlet chambers, either in or out of phase, or it may be controlled by an external pump supply providing either pulsatile or steady flow.

The apparatus shown in FIG. 1 may also be used for other purposes such as dialysis, e.g., as an artificial kidney. When so utilized, liquids of relatively high and relatively low concentrations of one or more of a group of molecules or ions in the higher concentration liquid passes through the wall of the membrane to the lower concentration liquid. In a similar manner, the apparatus may be used for washing blood cells or as a reverse osmosis device for concentrating or separating solute in or from solution.

The apparatus of the present invention may be constructed such that modular units comprising tubular membranes 2 and housing 1 may be stacked one upon another between the inlet chamber 5 and the outlet chamber 13.

Secondary flow characteristics may also be achieved by providing the tubular membranes with a configuration having changes in direction along its length such as U-shaped bends or the like.

We claim:

1. In an apparatus for modifying the properties of a fluid by adding or removing a substance in which said fluid flows through a tubular membrane capable of permitting a substance to pass therethrough, the improvement comprising the provision of an irregular configuration on the inner surface of the tubular membrane in a manner effective to create secondary flow in the fluid flowing through said tubular membrane such that the resistance to flow through said membrane is substantially reduced, said irregular configuration comprising spaced constrictions in the diameter of said tubular membrane and said tubular membranes having an unconstricted diameter of approximately ⅛ inch to ⅜ inch said constrictions maintained during the flow of fluid through said membrane by a plurality of rods which constrict the internal diameter of said membrane.

2. The apparatus of claim 1 wherein said rods are arranged in banks in which said rods are parallel to each other and in which at least some of said banks are angularly displaced with regard to other banks.

3. The apparatus of claim 1 wherein said membrane is mounted in a housing, said housing being provided with means for admitting a first fluid whereby said first fluid flows through said tubular membrane and means for admitting a second fluid whereby said second fluid flows around said tubular membrane.

4. The apparatus of claim 1 wherein means for imparting pulsatile flow to said fluid is provided.

5. The apparatus of claim 1 wherein heat exchange means for controlling the temperature of said fluid is provided.

6. The apparatus of claim 1 wherein said rods are staggered.

7. The apparatus of claim 1 wherein said irregular configuration comprises changes in direction of said tubular membrane.

* * * * *